United States Patent
Kim

[19]

[11] Patent Number: 6,098,626
[45] Date of Patent: Aug. 8, 2000

[54] CONDOM WITH MULTI-PURPOSE SEXUAL DEVICE

[76] Inventor: Hye-Sook Kim, 94-4, 3-Ga, Maesan-Ro Kwonseon-ku, Soowon-Si, Kyunggi-Do, Rep. of Korea

[21] Appl. No.: 09/302,020

[22] Filed: Apr. 29, 1999

[51] Int. Cl.$^7$ .................................................. A61F 6/04
[52] U.S. Cl. ............................................ 128/844; 128/918
[58] Field of Search .................................. 128/842, 844, 128/918; 604/347–353; 600/38, 39, 40

[56] References Cited

U.S. PATENT DOCUMENTS

| | | | |
|---|---|---|---|
| 5,331,974 | 7/1994 | Sook | 128/842 |
| 5,377,692 | 1/1995 | Pfeil | 128/918 |
| 5,454,379 | 10/1995 | Shepherd | 128/842 |
| 5,471,998 | 12/1995 | Kuyumciyan | 128/844 |
| 5,640,973 | 6/1997 | Blinn | 128/844 |
| 5,666,971 | 9/1997 | Anatolievich | 128/842 |

*Primary Examiner*—Michael A. Brown
*Attorney, Agent, or Firm*—Townend and Townsend and Crew LLP

[57] ABSTRACT

This invention relates to a condom having a hard case, an air hole formed at one side of an outer sheet at a rear end of the condom, and a tube for maintaining atmospheric pressure in the hard case and connecting the air hole with a nose of the hard case, the tube is located in an air inflation chamber which is defined by the hard case and said outer sheet thus the condom to perfecting not only contraception and preventing venereal disease but also aiding other sexual problems such as premature ejaculation and insufficient erection.

9 Claims, 12 Drawing Sheets

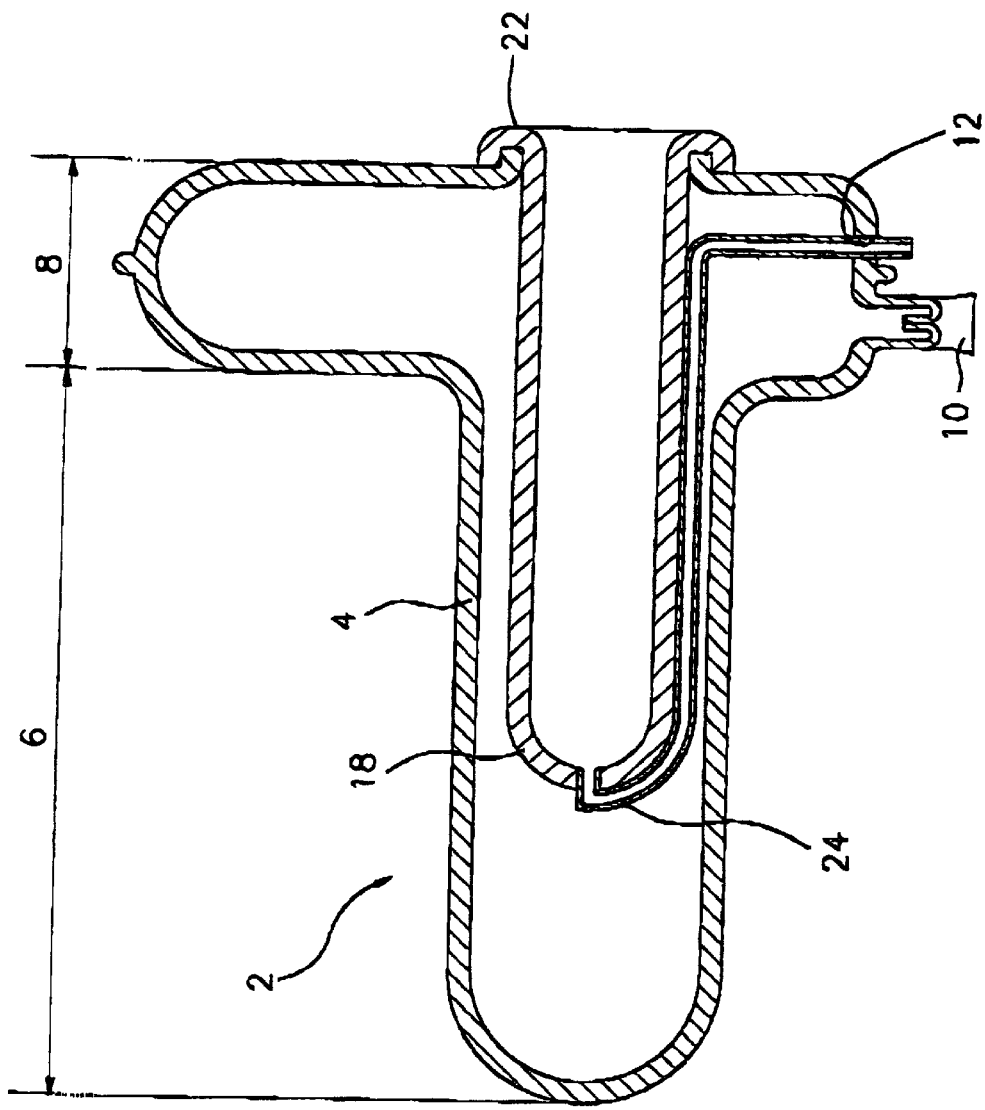

CONDOM WITH MULTI-PURPOSE SEXUAL DEVICE

BACKGROUND OF THE INVENTION

1. Field of the Invention

This invention relates to a condom, more particularly to perfecting not only contraception and preventing venereal disease but also aiding sexual problems such as premature ejaculation and insufficient erection.

2. Prior Art

In general, a condom is an essential device for contraception and preventing venereal disease.

One such device is disclosed in U.S. Pat. No. 5,331,974, of the applicant issued on Jul. 26, 1994. That condom comprises an inner sheet and outer sheet which are made of vinyl, and the outer sheet is defined by a forward insertion part and a rear pressure part. The pressure part has an air hole which fills with a proper amount of air blown between the inner and outer sheets. The inner sheet has a sealing line which prevents the inner sheet from reversing and detaching from the outer sheet.

The air is blown into the outer sheet by the air hole. The inner sheet is crumpled irregularly even though the outer sheet is inflated. Wearing of the condom is completed which the penis is inserted within the crumpled inner sheet.

The condom has at least one sealing line. After putting on the condom, it is difficult to insert the penis within the crumpled inner sheet due to the inflated outer sheet.

THE SUMMARY OF THE INVENTION

It is an object of the present invention to provide a condom consisting of a inner sheet which is not separated from the outer sheet and not detached from a user after being put on.

In respect of the procedure of wearing, this invention is improved over the prior art regarding insertion of the penis between the crumpled inner sheet with the inflating outer sheet.

Regarding production, this invention is manufactured through a very simple procedure except form a sealing line, as well as the cost for manufacturing the condom is better.

With regard to operational effect thereof, it has the feature of providing sexual satisfaction without a worry about infection due to venereal disease.

It is another object of this invention to provide a multi-purpose sexual device has a hard case with a solid formation for ease in wearing and helps to solve sexual problems such as premature ejaculation, incomplete erection, abnormal small penis size complex, etc.

To obtain the above objects, the condom according to a first preferred embodiment of the present invention comprises: a hard case sized and shaped to fit around a penis; an air hole formed at one side of an outer sheet at a rear end of the condom, the outer sheet inflatably surrounds the hard case and form-fitted at the opening of the hard case; and a tube for maintaining atmospheric pressure in the hard case and connecting the air hole with a nose of the hard case, the tube is located in an air inflation chamber which is defined by the hard case and said outer sheet.

The condom further comprises a harness for a user to wear the condom.

The condom comprises a means for defining both an insertion part in the forward area of the condom and a pressure part having an oblong shape in the backward area of the condom, the pressure part has a holding slot oblong vertex area thereat and the harness capable of being attached thereto.

The harness comprises a pair of wearing belts having a buckle for belting onto the user; plural attaching belts formed at a center area of the wearing belt, the length of attaching belts is variable; and a holder formed at an end of the attaching belts and holding the holding slot which is formed at the pressure part.

The attaching belt comprises a means for defining both forward attaching belts plurally which are located on a front side of the user, and at least one backward attaching belt which is located at a back side of the user, the backward attaching belt has a plate for preventing insertion of the backward attaching belt into the anus and located perpendicular thereat. The plate has pairs of slits in which the at least one backward attaching belt is passed therethrough respectively.

BRIEF DESCRIPTION OF THE DRAWINGS

This invention will be better understood and its various objects and advantages will be more fully appreciated from the following description taken in conjunction with the accompanying drawings, in which:

FIG. 1 is a side-sectional view of the inflated state according to a preferred embodiment of the present invention;

DETAILED DESCRIPTION OF THE PREFERRED EMBODIMENT

Figure 2A:
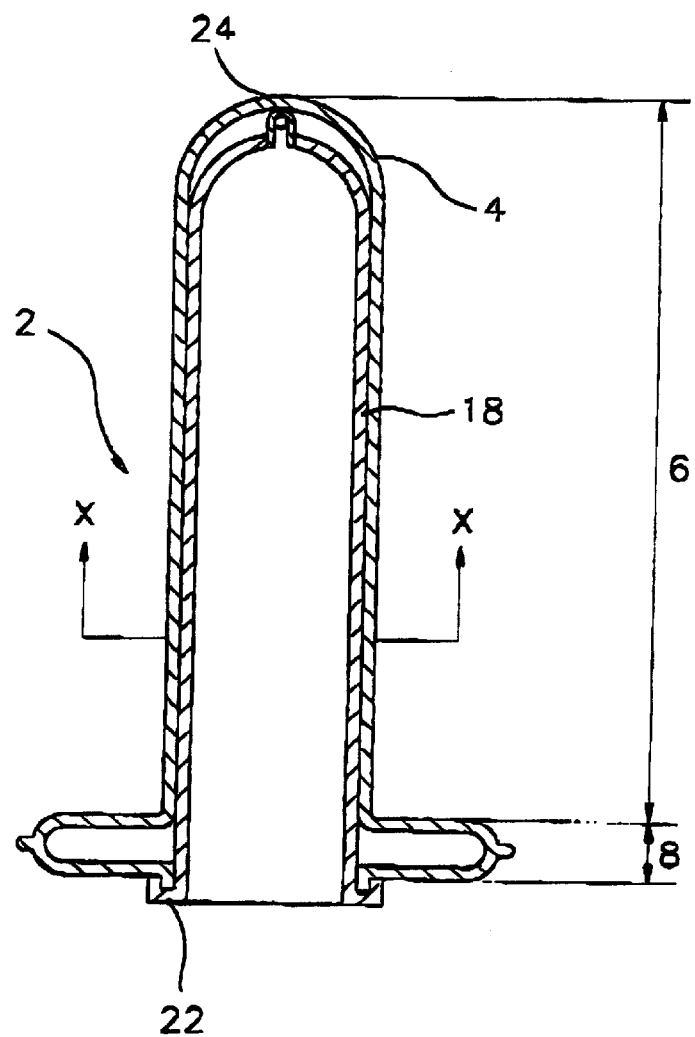
FIG. 2A is a side-sectional view of the deflated state according to a preferred embodiment of the present invention.

Hereinafter, this invention will be described in detail with reference to the drawings.

FIG. 1 is a side sectional view of the inflated state of a condom according to the present invention.

As shown in FIG. 1, the condom 2 comprises an outer sheet 4 which is made of a vinyl or latex, a hard case 18 is form-fitted and shaped to fit around a penis, the hard case 18 is made of a solid material, for example aluminum, and a tube 24 for maintaining atmospheric pressure in the hard case 18.

The outer sheet 4 and the hard case 18 define an air inflation chamber, an end side of the opening of the hard case 18 forms a bending portion 22 for form-fitting the outer sheet 4. Thus the outer sheet 4 and the hard case 18 are formed together in the same body. The composition and function of an air inflation valve 10 is the same as disclosed in the prior art.

The outer sheet 4 of the condom 2 is capable of defining both an insertion part 6 which is inserted into the vagina and a pressure part 8 lengthened from the insertion part 6, wherein the pressure part 8 is located on the pubis. The insertion part 6 and the pressure part 8 are inflable by an air inflation valve 10 for receiving blown air.

An air hole 12 forms at one side of an outer sheet 4 at a rear end of the condom 2. A tube 24 connects the air hole 12 with a nose of the hard case 18. The tube 24 is located in the air inflation chamber.

FIGS. 2A through 4B show the deflated state of the condom 2.

Figure 2B:
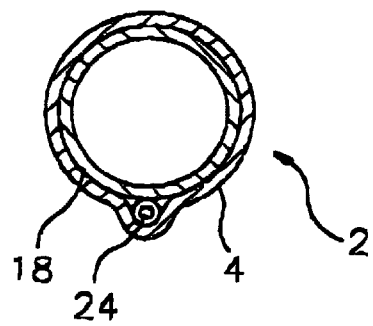
FIG. 2B is a sectional view of the X—X line of the FIG. 2A.

As shown in FIG. 2A, the outer sheet 4 adheres to the hard case 18 closely because the air is blown out. The hard case 18 has rigid formation. The tube 24 projects into the outer sheet 4 as shown in FIG. 2B.

Figure 3:
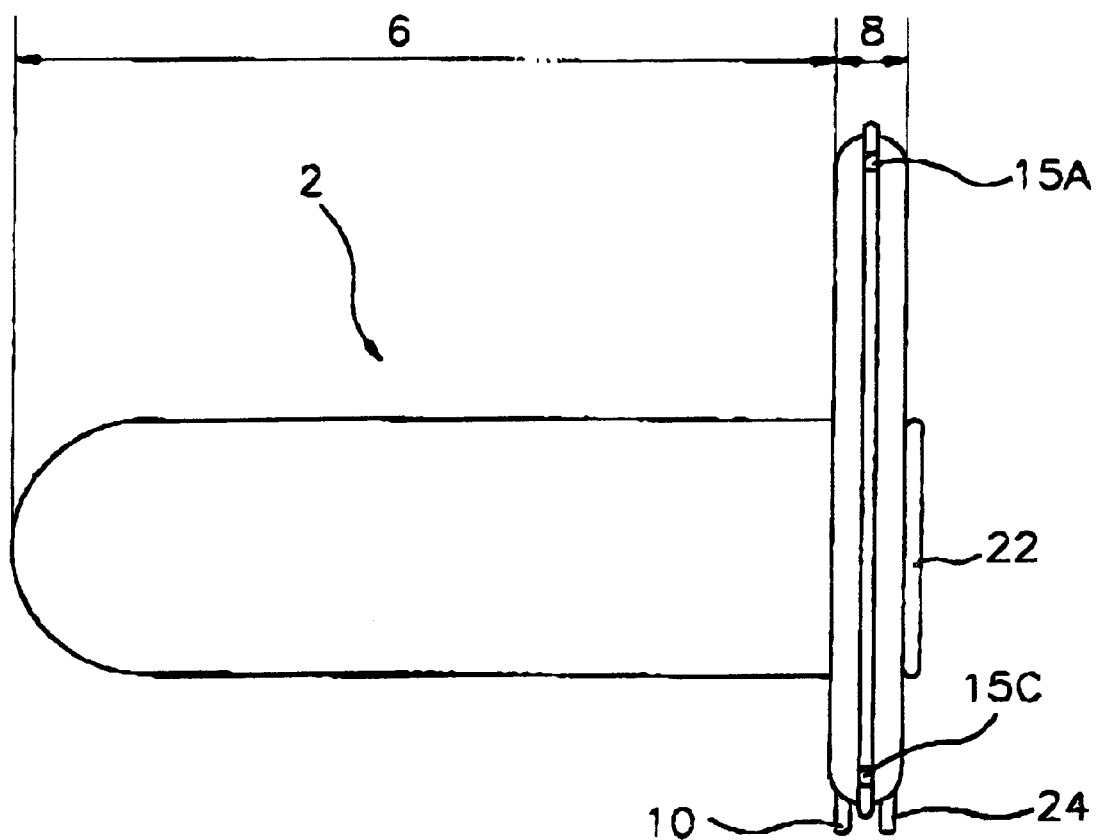
FIGS. 3 to 4B are side views of the deflated state according to a preferred embodiment of the present invention.

As shown in FIG. 3, the pressure part 8 maintains shape naturally, and holding slots 15A, 15B are formed at the vertex area of the pressure part 8 sides. The tube 24 protrudes from the air hole 12 and the air inflation valve 10 as shown in the FIGS. 4A and 4B.

Figure 4A:
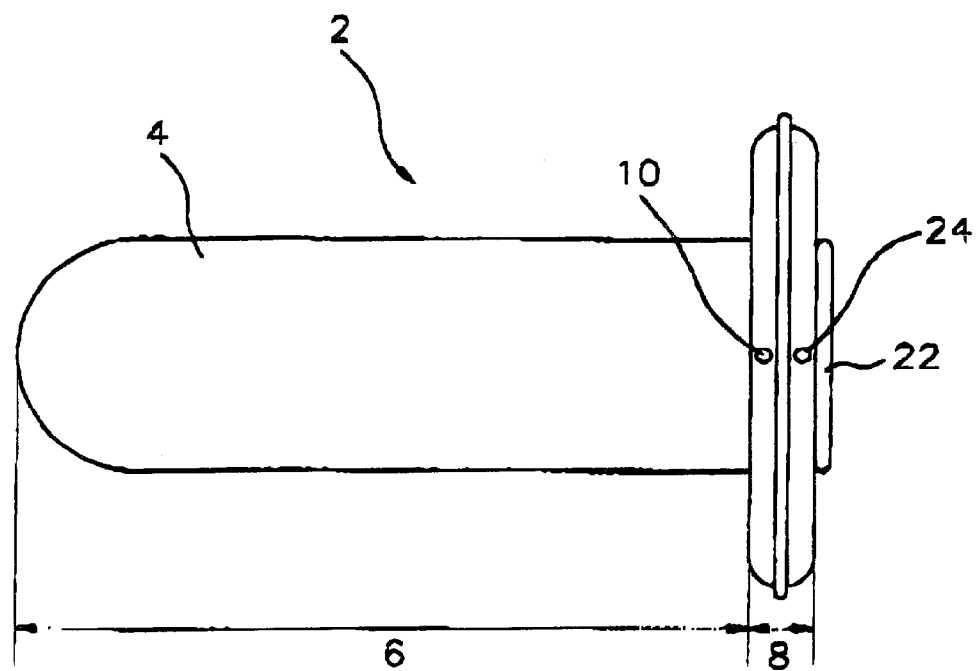
Figure 4B:
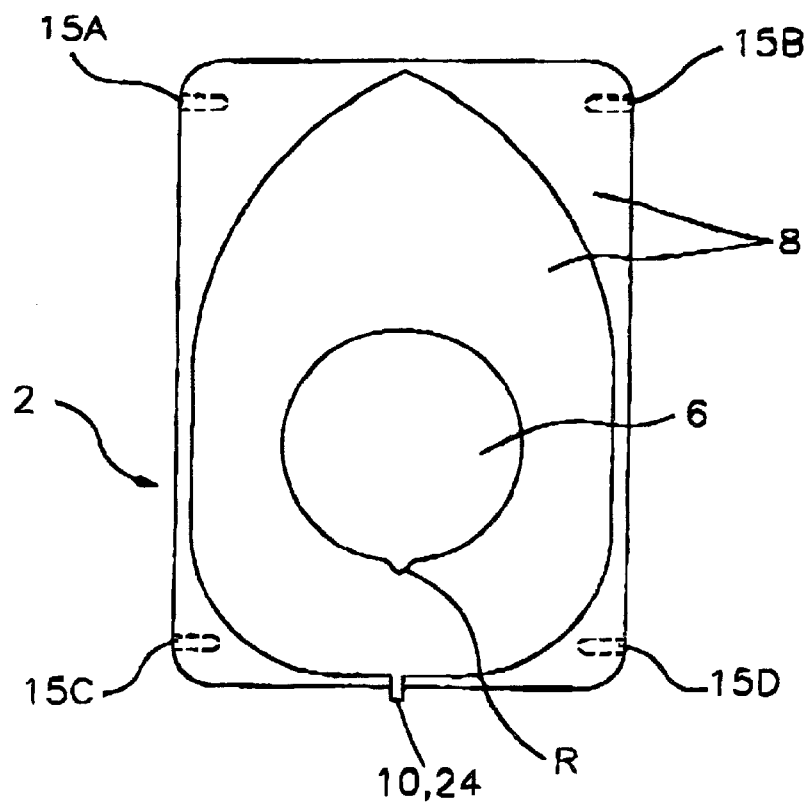

The pressure part 8 is oblong shaped as shown in FIG. 4B.

The holding slots 15A, 15B, 15C, 15D are formed at edges of the pressure part 8. The reference character R indicates projection of the outer sheet 4 because of the tube 24.

As a way of wearing the condom 2, the air is blown through the air inflation valve 10 so the outer sheet 4 is inflated.

Upon inflation of the outer sheet 4, the hard case 18 and the outer sheet 4 define the air inflation chamber. The pressure of the air inflation chamber presses upon the outer sheet 4 only. The hard case 18 has rigidity to prevent deformation.

The tube 24 which is located in the air inflation chamber maintains an atmospheric pressure within the hard case 18. When the condom 2 is worn, the penis depresses the air in the hard case 18 upon insertion thereinto. The depressed air is released from the condom 2 to the exterior. If the tube 24 is not formed, insertion of the penis into hard case is difficult 18 since the depressed air re-presses the penis. This tube 24 also maintains a specific air pressure after insertion of the penis into the hard case 18, but varying according to the penis size.

The hard case 18 can be manufactured in variable sizes.

Figure 5:
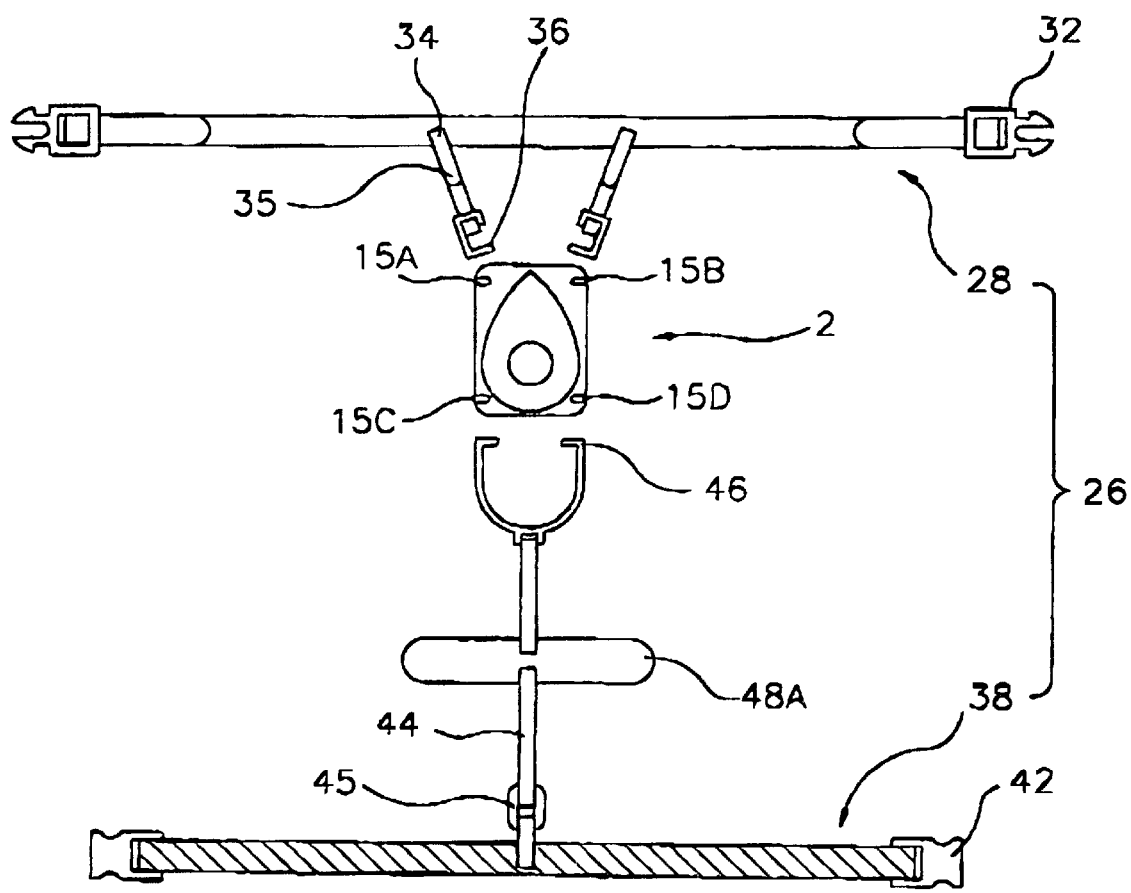
FIG. 5 is a plane view of a harness according to a preferred embodiment of the present invention.

The hard case can be detached by the user. As shown in FIG. 5, the condom has a harness 26 for preventing detachment.

The harness 26 comprises a pair of wearing belts 28,38 each having a buckle 32,42 for belting onto the user, plural attaching belts 34,44 formed at a center area of the wearing belts 28,38, and each holder 36,46 formed at an end of the attaching belts 34,44 and holding the holding slots 15A, 15B,15C,15D which are formed at the pressure part 8.

The attaching belts 34,44 comprise a means for defining both forward attaching belts 34 plurally which are located on a front side of the user and at least one backward attaching belt 44 which is located at a back side of the user. The backward attaching belt 44 has a plate 48A for preventing insertion of the backward attach belt 44 into the anus and located perpendicular thereat.

Figure 6:
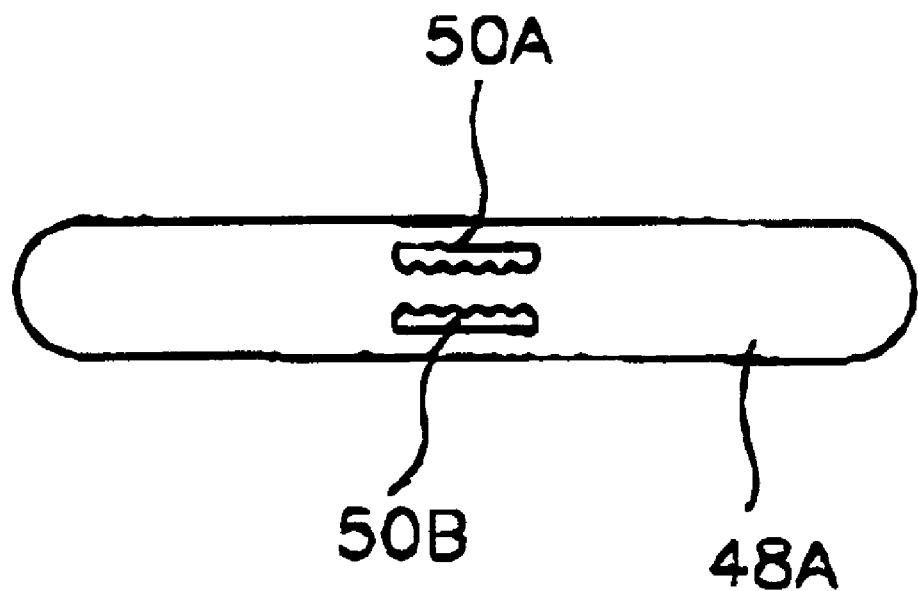
FIG. 6 is a plane view of a plate according to the first preferred embodiment of the present invention.

As shown in FIG. 6, the plate 48A has a pair of slits 50A,50B through which the backward attaching belt 44 passes and can be attached. The slits 50A,50B of the plate 48A have saw teeth for fixing the location of the plate 48A.

Figure 7A:
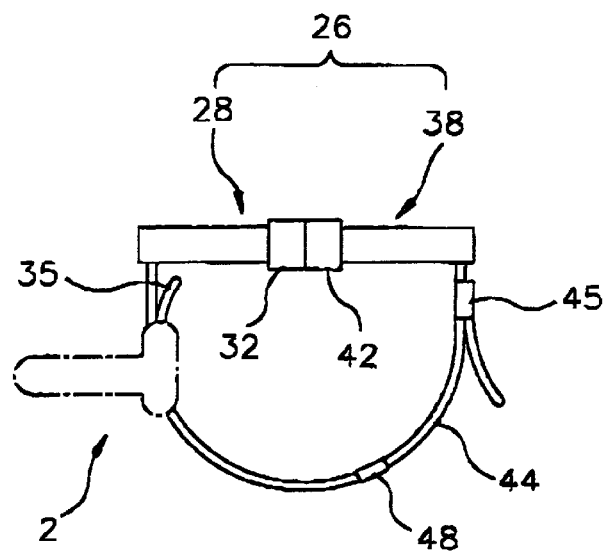
FIGS. 7A and 7B show use of the harness according to the present invention.
Figure 7B:
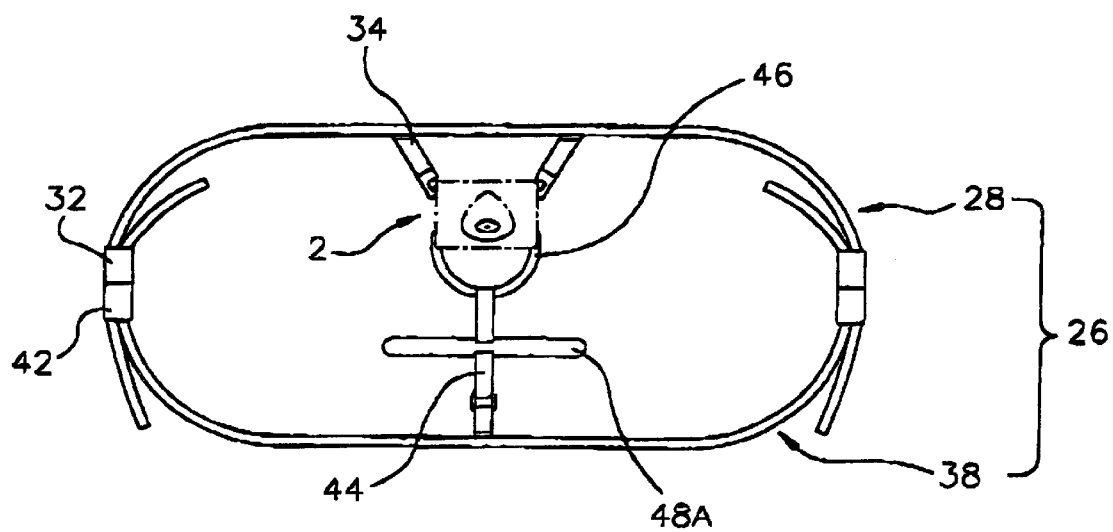

The use of the harness 26 is shown in FIGS. 7A and 7B.

A pair of wearing belts 28,38 are belted to the user and fixed by the buckles 32,42. The location of the buckles 32,42 are at the front waist side of the user for convenience of use.

The holder 36,46 is inserted into the holding slots 15A, 15B,15C,15D respectively. Therefore to complete putting on the condom 2 by the user, the attaching belts 34,44 are puts at a set length by use of velcro-tape 35 and belt gripper 45.

Figure 8A:
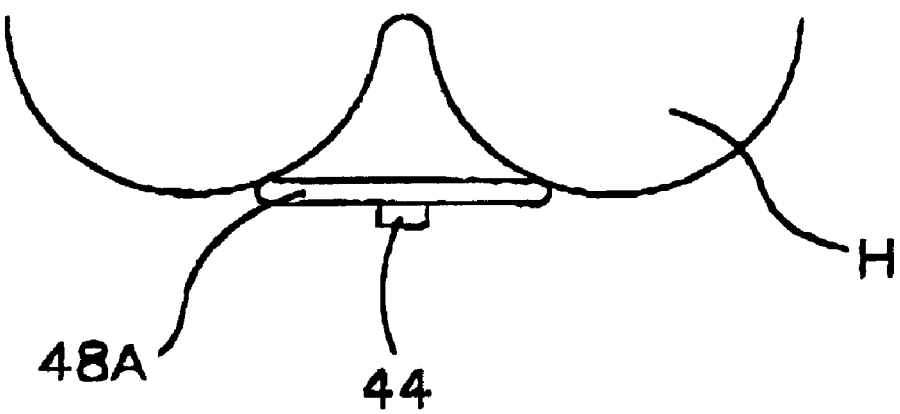
FIG. 8A shows use of the plate according to the first embodiment of the present invention.
Figure 8B:
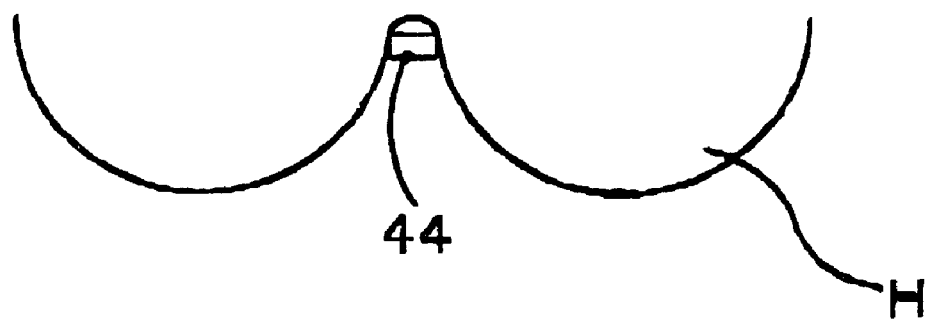
FIG. 8B shows the use of the harness except for the plate.

The forward attaching belt 34 is located on a front side of the user, and the backward attaching belt 44 is located between the hips H at the anus. As shown in FIG. 8A, the plate 48A prevents the backward attaching belt 44 from being inserted into the anus. Therefore, without use of the plate 48A shown in FIG. 8B, the backward attaching belt 44 would touch and insert into the anus, thus resulting in the skin of the anus being injured when the harness 26 is shaken or moved.

Figure 9A:
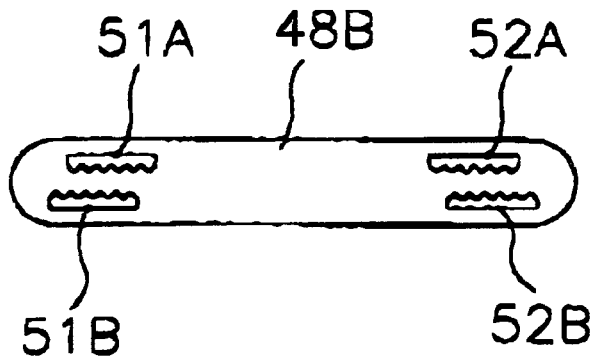
FIG. 9A is a plane view of the plate according to the second embodiment of the present invention.
Figure 9B:
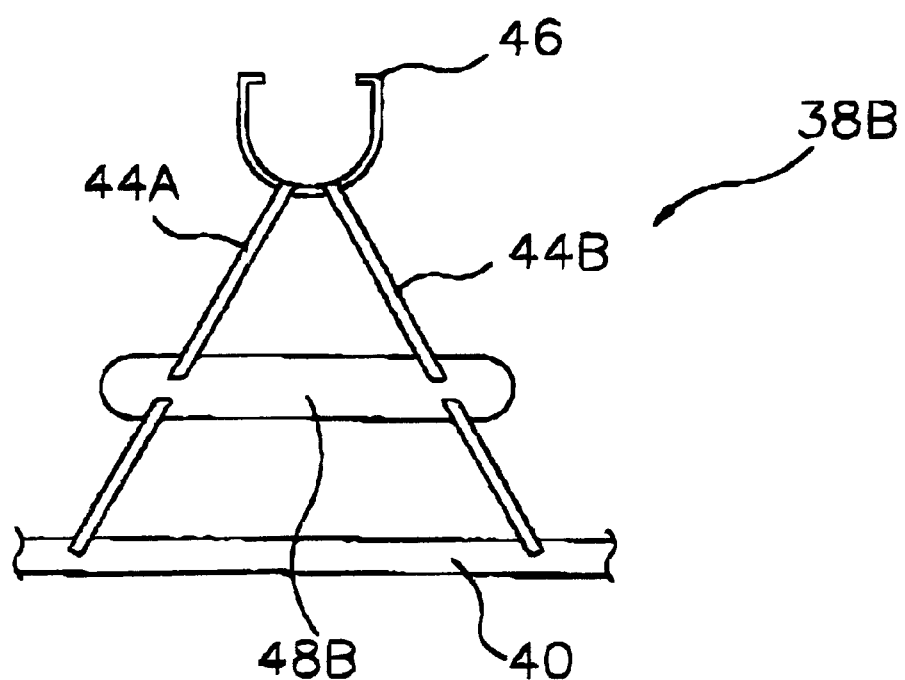
FIG. 9B is an attaching state view of the plate according to the second embodiment of the present invention.
Figure 10:
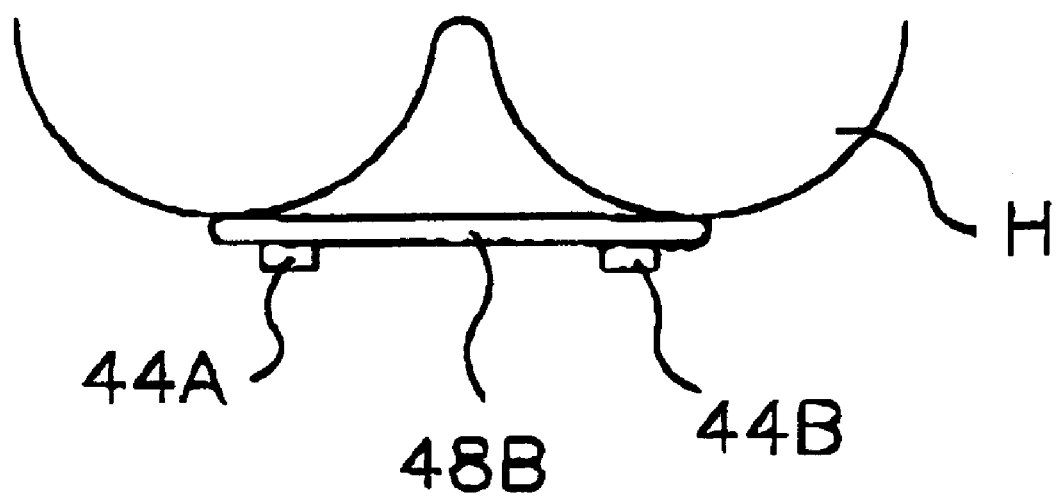
FIG. 10 shows use of the plate according to second embodiment of the present invention.

Meanwhile, another embodiment of the plate 48B according to the backward attaching belts 44A,44B are shown in FIGS. 9A and 9B. As shown in FIG. 9B, two backward attaching belts 44A,44B are radially used, thus the slits 51A,51B,52A,52B have two pairs which are formed on the plate 48B. The use of the plate 48B shown in FIG. 10, prevents the backward attaching belts 44A, 44B from being inserted into the gap of the hips for improved wearing of the condom. Therefore, the perfection of the condom 2 being worn by the user also has the features of overcoming the several phenomena common to the male population such as premature ejaculation, incomplete erection, along with providing perfect sexual satisfaction without worry about infection of venereal disease.

the condom 2 may incorporate an extra device as shown in FIGS. 11A through 12B.

Figure 11A:
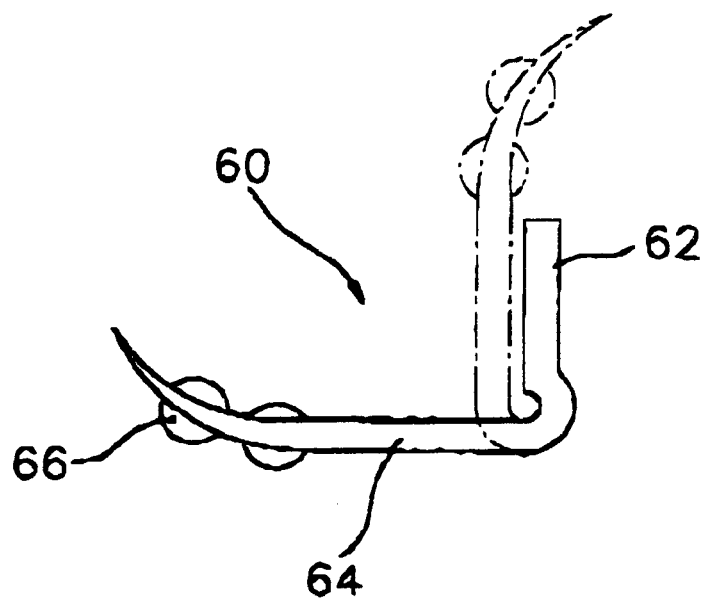
FIG. 11A is a side view of a roller device according to the present invention.
Figure 11B:
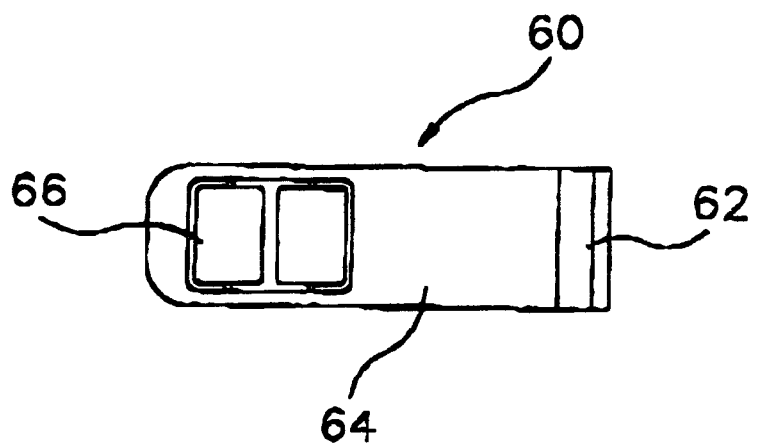
FIG. 11B is a plane view of the roller device according to the present invention.

A roller device 60 shown in FIGS. 11A and 11B, consists of a flexible plate 64 having a roller 66 which is made of rubber and an attaching portion 62 formed with the flexible plate 64 and attached to the condom 2 by way of rubber band or glue. The roller 66 attaches to the clitoris and the flexible plate 64 is flexible for overcoming sexual problems.

Figure 12A:
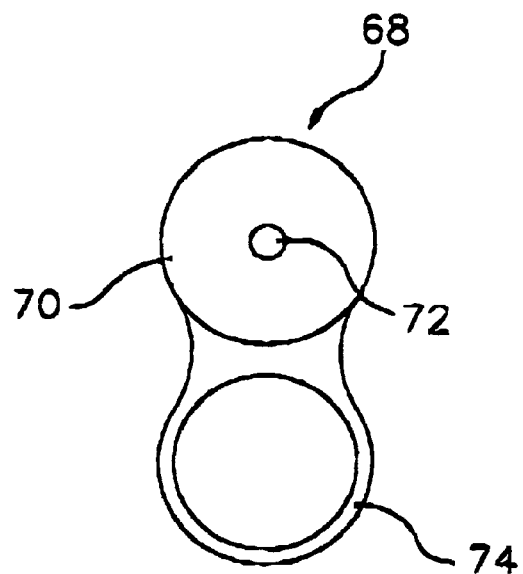
FIG. 12A is a front view of a bumper device according to the present invention.
Figure 12B:
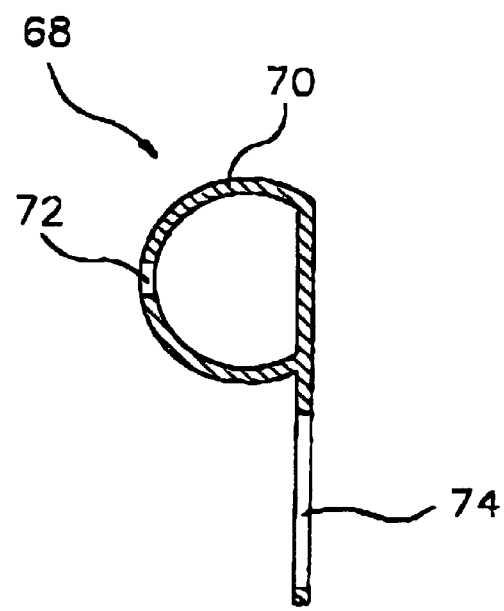
FIG. 12B is a side-sectional view of the bumper device according to the present invention.

A bumper device 68 a shown in FIGS. 12A and 12B, consists of a bladder 70 having a hole 72 formed in a front thereof, and a ring portion 74 which is lengthened from the bladder 70 and inserted into the condom 2.

The roller device 60 and bumper device 68 can be used independent of the condom 2.

While this invention has been particularly shown and described with reference to particular embodiments thereof, it will be understood by those skilled in the art that various changes in form and details may be effected therein without departing from the spirit and scope of the invention as defined by the appended claims.

What is claimed is:

1. A condom which can be used as a multi-purpose sexual device, said condom comprising:

a hard case sized and shaped to fit around a penis;

an air hole formed at one side of an outer sheet at a rear end of the condom, said outer sheet inflatably surrounding said hard case and form-fitted at an opening of said hard case; and a tube for maintaining atmospheric pressure in said hard case and connecting said air hole with a nose of said hard case, said tube being located in an air inflation chamber which is defined by said hard case and said outer sheet.

2. The condom as claimed in claim 1, wherein said hard case is made of aluminum.

3. The condom as claimed in claim 1, further comprising a harness for a user to wear said condom.

4. The condom as claimed in claim 3, wherein said condom comprises a means for defining both an insertion part in the forward area of said condom and a pressure part with an oblong shape in the backward area of said condom, said pressure part having a holding slot oblong vertex area thereat and said harness capable of being attached thereto.

5. The condom as claimed in claim 4, wherein said harness comprises;

a pair of wearing belts having a buckle for belting onto the user;

plural attaching belts formed at a center area of said wearing belt; and a holder formed at an end of said attaching belt and holding said holding slot which is formed at said pressure part.

6. The condom as claimed in claim 5, wherein said attaching belt comprises a means for defining both forward attaching belts plurally which are located on a front side of the user and at least one backward attaching belt which is located at a back side of the user, said backward attaching belt having a plate for preventing insertion of said backward attaching belt into anus and located perpendicular thereat.

7. The condom as claimed in clam 6, wherein said plate having pairs of slits in which said at least one backward attaching belt is passed therethrough respectively.

8. The condom as claimed in claim 1, wherein said condom further comprises a roller device, said roller device consisting of;

a flexible plate having a roller which is made of rubber; and an attaching portion formed with said flexible plate and attached to said condom.

9. The condom as claimed in claim 1, wherein said condom further comprises a bumper device, said bumper device consisting of;

a bladder having a hole formed in a front thereof; and a ring portion which is lengthened from said bladder and inserted into said condom.

* * * * *